US009823223B2

(12) United States Patent
Harrison et al.

(10) Patent No.: US 9,823,223 B2
(45) Date of Patent: Nov. 21, 2017

(54) MEASURING A DEW POINT

(71) Applicant: Schlumberger Technology Corporation, Sugar Land, TX (US)

(72) Inventors: Christopher Harrison, Auburndale, MA (US); Shunsuke Fukagawa, Arlington, MA (US); Matthew T. Sullivan, Westwood, MA (US); Elizabeth Jennings Smythe, Cambridge, MA (US); John Meier, Boston, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 93 days.

(21) Appl. No.: 14/847,012

(22) Filed: Sep. 8, 2015

(65) Prior Publication Data
US 2016/0091462 A1 Mar. 31, 2016

Related U.S. Application Data

(60) Provisional application No. 62/054,986, filed on Sep. 25, 2014.

(51) Int. Cl.
G01N 29/036 (2006.01)
G01N 11/16 (2006.01)

(52) U.S. Cl.
CPC .......... *G01N 29/036* (2013.01); *G01N 11/16* (2013.01); *G01N 2291/014* (2013.01); *G01N 2291/02818* (2013.01); *G01N 2291/02845* (2013.01)

(58) Field of Classification Search
CPC ................ G01N 29/036; G01N 11/16; G01N 2291/014; G01N 2291/02818; G01N 2291/02845
See application file for complete search history.

(56) References Cited

U.S. PATENT DOCUMENTS

| | | |
|---|---|---|
| 7,574,898 B2 | 8/2009 | Harrison et al. |
| 7,784,330 B2 | 8/2010 | Angelescu et al. |
| 2003/0033866 A1 | 2/2003 | Diakonov et al. |
| 2003/0205083 A1 | 11/2003 | Tubel et al. |
| 2009/0120168 A1 | 5/2009 | Harrison et al. |
| 2010/0006284 A1 | 1/2010 | Sonne et al. |
| 2013/0110401 A1 | 5/2013 | Hsu et al. |
| 2014/0033816 A1 | 2/2014 | Goodwin |

OTHER PUBLICATIONS

Li Fan, et al., "Understanding Gas-condensate Reservoirs," Oilfield Review Winter 2005/2006, pp. 14-27.

I. Etchart, et al, "A Comparison of Both Steady State Resonance and Transient Decay Methods of Determining Viscosity with a Vibrating Wire Viscometer: Results for Certified Reference Fluids for Viscosity that are Stagnant with Viscosity between (2.5 and 66) mPa/s and Flowing ag Volumetric Flow Rates Below 50 cm3/2-1 and Viscosities Less than 34 mPa.s," Journal of Chemical & Engineering Data 2008, vol. 53, pp. 1691-1697.

(Continued)

*Primary Examiner* — Hezron E Williams
*Assistant Examiner* — David Z Huang
(74) *Attorney, Agent, or Firm* — Trevor G. Grove

(57) ABSTRACT

A sensor including a vibrating wire is used to measure a dew point of a fluid.

6 Claims, 4 Drawing Sheets

(56) References Cited

OTHER PUBLICATIONS

M. Kandil, "The Development of a Vibrating Wire Viscometer and a Microwave Cavity Resonator for the Measurement of Viscosity, Dew Points, Density, and Liguid Volume Fraction at High Temperature and Pressure—A Thesis Submitted in Partial Fulfilment of the Requirements for the Degree of Doctor of Philosophy," University of Canterbury, 2005.
"Retrograde Condensation," from Wikipedia, retrieved on Sep. 3, 2014.
International search report for the equivalent PCT patent application No. PCT/US2015/051301 dated Jan. 8, 2016.

MEASURING A DEW POINT

CROSS REFERENCE TO RELATED APPLICATIONS

This is a non provisional patent application of co-pending U.S. provisional patent application Ser. No. 62/054,986 to Christopher Harrison, et al filed on Sep. 25, 2014, which is hereby incorporated in its entirety for all intents and purposes by this reference.

BACKGROUND

Measurement of a physical property of a fluid can be performed for various purposes. In the oil and gas industry, the measured physical property of a fluid can be beneficial in understanding characteristics of the fluid, which aid in decision-making with respect to hydrocarbon production, reservoir exploration, and so forth.

BRIEF DESCRIPTION OF THE DRAWINGS

Some implementations are described with respect to the following figures.

SUMMARY

In accordance with some implementations, a sensor including a vibrating wire is used to measure a dew point of a fluid.

Other or alternative features will become apparent from the following description, from the drawings, and from the claims.

DETAILED DESCRIPTION

A physical property of a fluid that may be useful for various purposes is a dew point of a fluid, where a dew point can refer to the pressure at which condensation of the fluid starts to occur. The fluid can be a retrograde condensate. Reduction of pressure of a retrograde condensate can result in condensation of the fluid when the pressure is reduced to below the dew point of the retrograde condensate.

Determining the dew point of a fluid can be useful for enhancing hydrocarbon production through a well from a hydrocarbon reservoir in a subsurface structure. As an example, a well can be used to produce natural gas from a gas-condensate reservoir in the subsurface structure. Gas production using the well can involve drawing down the pressure of the well. If the pressure drawdown causes the pressure in the well to drop below a dew point of the gas, then condensation of the gas can occur. This condensation can lead to restrictions in the flow of gas in the well. This phenomenon is referred to as condensate blockage or condensate banking and can reduce the productivity of the well.

In other examples, detecting a dew point of a fluid can be useful in other applications.

Traditional techniques for dew point detection include optical detection techniques, in which condensation of dew droplets in a fluid sample can lead to scattering of light that can be detected by optical sensors. However, optical detection techniques can be complex and/or expensive.

Figure 1:
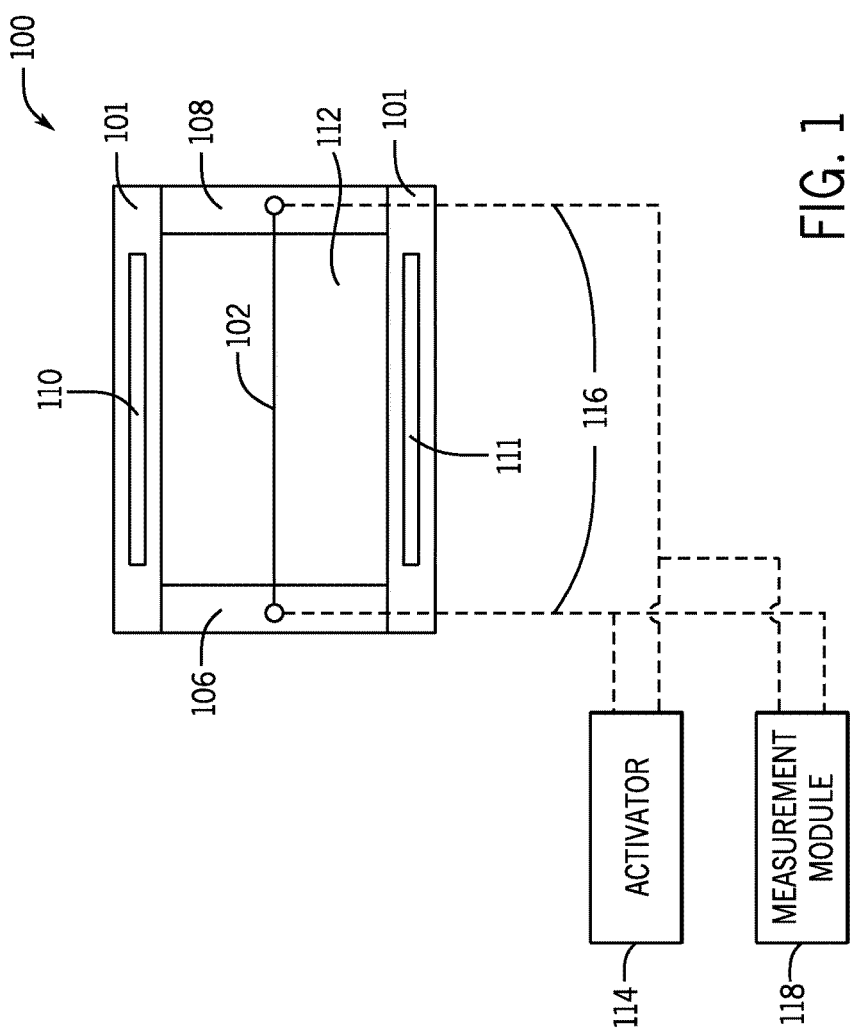
FIG. 1 is a schematic diagram of an example arrangement that includes a vibrating wire viscometer for measuring a dew point of a fluid, according to some implementations.

In accordance with some implementations, a sensor device that includes a vibrating wire is used for measuring a dew point of a fluid. This type of sensor device can be referred to as a vibrating wire viscometer. FIG. 1 shows an example of a vibrating wire viscometer 100 that includes an electrically conductive wire 102 that is held in tension by support structures 106 and 108. In some examples, the wire 102 can have a diameter that is less than 200 micrometers ($\mu m$). In other examples, the wire 102 can have other diameters.

The vibrating wire viscometer 100 also includes an outer housing 101 that defines a sealed inner chamber 112 that contains a fluid, such as a retrograde condensate. The fluid can be introduced into the chamber through a fluid conduit (not shown) attached to the vibrating wire viscometer 100. The vibrating wire 102, which is immersed in the fluid that is contained in the chamber 112, is able to detect a dew point of the fluid.

An activator 114 is coupled to the wire 102 over communication lines 116. The activator 114 can include a signal driver that is able to cause an electrical current to pass through the vibrating wire 102. The vibrating wire 102 can be formed of an electrically conductive material, and is capable of displacements from an initial position in response to electrical current being passed through the wire 102 in the presence of a magnetic field produced by one or more magnetic elements, such as magnetic elements 110 and 111 shown in FIG. 1. In some examples, the magnetic elements 110 and 111 can include electromagnetic elements that produce a magnetic field when the electromagnetic elements are energized (such as by the activator 114).

The electrical current that is passed through the vibrating wire 102 can be an oscillating electrical current. The combination of the oscillating electrical current in the wire 102 and the magnetic field produced by the magnetic elements 110 and 111 creates an oscillating force (according to the Lorentz force law) that causes vibratory movement of the wire 102.

In some examples, the activator 114 can drive an electrical current into the vibrating wire 102 to cause resonance and thus vibratory movement of the vibrating wire 102. Subsequently, the activator 114 can extinguish the excitation of the vibrating wire 102 by removing the electrical current from the vibrating wire 102.

Once excitation of the vibrating wire 102 is removed, the vibrating wire 102 continues to exhibit vibratory movement that rings down over time. The ringdown of the vibrating wire 102 can be monitored over the communication lines 116 by a measurement module 118 connected to the vibrating wire 102. The motion of the vibrating wire 102 in the presence of the magnetic field leads to a small voltage (according to Faraday's law) that can be measured and recorded by the measurement module 118 over the communication lines 116.

Although FIG. 1 depicts the same communication lines 116 coupling the activator 114 and the measurement module 118 to the vibrating wire 102, it is noted that in other examples, the activator 114 and measurement module 118 can be coupled over respective different communication lines to the vibrating wire 102.

The vibrating wire 102 can act as a nucleation site for condensation droplets (dew droplets), such that the dew droplets coat the wire 102. The presence of the dew droplets on the vibrating wire 102 adds a mass to the vibrating wire 102 and lowers the resonant frequency and also increases the damping experienced by the vibrating wire 102. Thus, the vibrating wire 102 will exhibit a vibratory motion according to a first signature when dew droplets are not present on the vibrating wire 102, but the vibrating wire 102 will exhibit vibratory motion according to a second, different signature when dew droplets are present on the vibrating wire 102. The specific signature of a vibratory motion detected by the vibrating wire viscometer 100 can be compared to the first and second signatures to determine when condensation has occurred, such that the dew point (the pressure at which condensation occurs) can be detected.

Figure 2A:
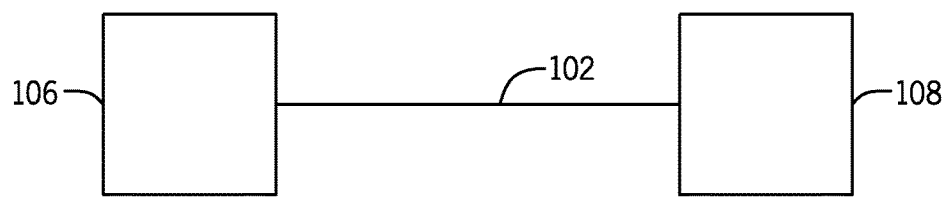
FIGS. 2A-2C are schematic diagrams illustrating movement of the vibrating wire, according to some implementations.
Figure 2B:
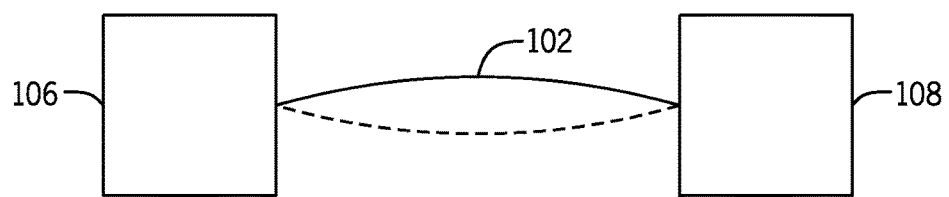
Figure 2C:
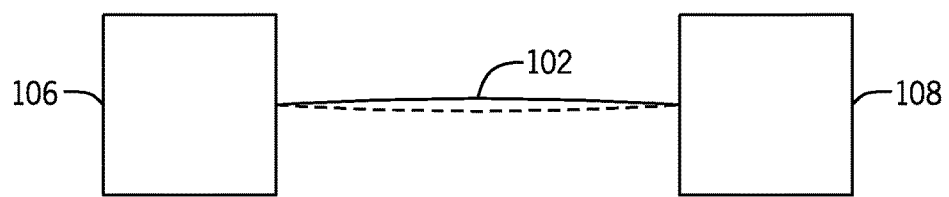

FIGS. 2A-2C are schematic diagrams that illustrate three respective different states of the vibrating wire 102. FIG. 2A shows the vibrating wire 102 (between support structures 106 and 108) at an initial steady state position (when the wire 102 is not vibrating), prior to the vibrating wire 102 being energized by the activator 114.

FIG. 2B shows vibration of the vibrating wire 102 with a relatively large amplitude and high quality factor (the term "quality factor" will be discussed further below), caused by energization of the vibrating wire 102 by the activator 114. FIG. 2B shows vibrating movement of the vibrating wire 102 when condensation of the fluid in the chamber 112 of FIG. 1 has not yet occurred (under a condition in which the pressure in the chamber 112 is greater than the dew point).

FIG. 2C shows vibrating movement of the vibrating wire 102 in the presence of condensation of the fluid (under a condition in which the pressure in the chamber 112 has been lowered below the dew point). Although not shown in FIG. 2C, dew droplets have formed on the vibrating wire 102 of FIG. 2C. The amplitude and quality factor of the vibration of the vibrating wire 102 has been dampened due to the added mass of the dew droplets on the vibrating wire 102.

As noted above, in some implementations, measurement of the induced vibratory motion of the vibrating wire 102 is performed after the excitation produced by the activator 114 has been removed (i.e. electrical current is no longer driven through the vibrating wire 102). The transient mode ringdown (after removal of excitation) of the vibrating wire 102 can be in the form of an exponential decay of the oscillation envelope.

Figure 3:
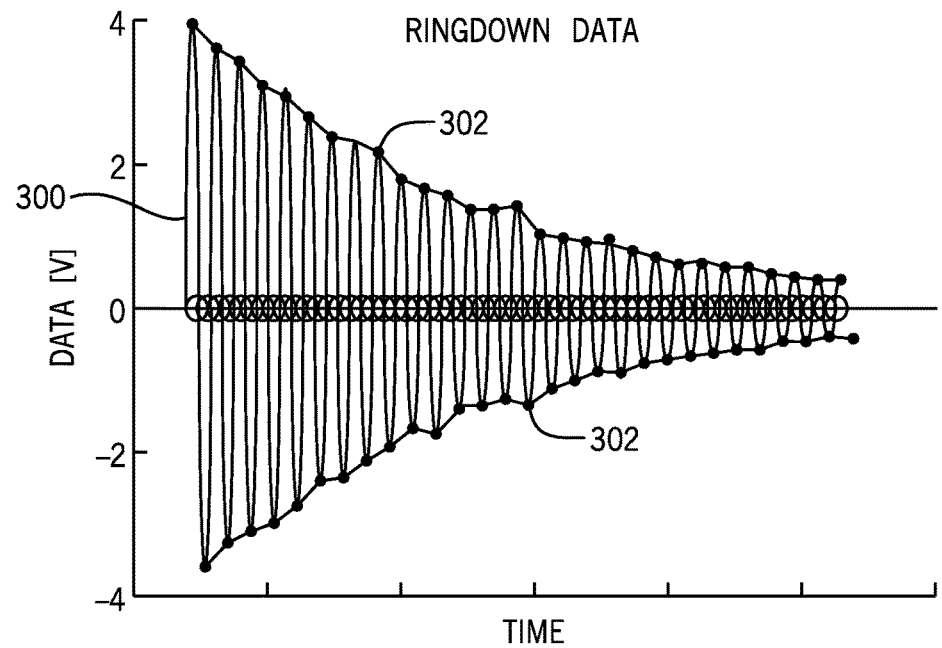
FIG. 3 is a chart depicting ringdown of the vibrating wire, according to some implementations.

FIG. 3 is a chart that depicts an example of ringdown data detected by the measurement module 118 after excitation has been removed. The chart depicts the voltage (vertical axis) of an oscillating signal 300 as a function of time (horizontal axis). Over time, after excitation of the vibrating wire 102 has been removed, the amplitude of the oscillating signal decays generally exponentially according to an oscillation envelope 302.

In the transient mode (after excitation has been removed from the vibrating wire 102), the induced voltage V(t) developed across the wire 102 can be a short-lived oscillation that varies as a function of time (t) and conforms to a simple damped harmonic model for small amplitude, expressed as:

$$V(t)=V_0 e^{-\Delta \omega t} \sin(\omega t+\phi), \quad \text{(Eq. 1)}$$

where $V_0$ is the initial amplitude of the transient signal, $\Delta$ is the decrement controlling the damping of the motion of the wire 102, $\omega$ is the angular resonance frequency of the wire 102, and $\phi$ is the unknown phase angle.

Note that the logarithmic decrement is a parameter for characterizing the energy loss of a resonator, and can be expressed as $2\pi\Delta$. In the present disclosure, $\Delta$ is referred to as the decrement (as opposed to the logarithmic decrement).

In Eq. 1, the decrement $\Delta$ is related to the properties of both the wire 102 and fluid that surrounds the wire 102, according to the following expression:

$$\Delta = \frac{(\rho/\rho_s)k' + 2\Delta_0}{2[1+(\rho/\rho_s)k]}, \quad \text{(Eq. 2)}$$

where $\rho$ and $\rho_s$ represent the density of the fluid and the density of the wire 102, respectively, $\Delta_0$ represents the internal damping of the wire 102 in a vacuum, and k and k' are defined as $$k=1+2T(A), \quad \text{(Eq. 3)}$$

$$k'=2R(A)+2\Delta T(A). \quad \text{(Eq. 4)}$$

In Eqs. 3 and 4, where R(A) and T(A) denote, respectively, the real part and imaginary part of a complex quantity A. The complex quantity A in can be expressed as $$A = (i-\Delta)\left[1 + \frac{2K_1\left[\{(i-\Delta)\Omega\}^{\frac{1}{2}}\right]}{[(i-\Delta)\Omega]^{\frac{1}{2}} K_0\left[\{(i-\Delta)\Omega\}^{\frac{1}{2}}\right]}\right]. \quad \text{(Eq. 5)}$$

where $K_0$ and $K_1$ are modified Bessel functions of the second order. The parameter $\Omega$ is a modified Reynolds number that characterizes the flow around the cylindrical wire 102 of radius R at the resonance frequency $\omega$, and is given by:

$$\Omega = \frac{\omega \rho R^2}{\eta} \quad \text{(Eq. 6)}$$

where $\eta$ represents the viscosity of the fluid surrounding the wire 102.

When using an actuating signal having a voltage and current, and a conductive vibrating wire to which this actuating signal is applied, the vibrating wire and any stationary wire or cables used to deliver this actuating signal have an electrical impedance that gives rise to a background voltage so that the measured voltage may not equal to that given by Eq. 1 above. Accordingly, Eq. 1 is modified to accommodate the finite impedance to give $$V(t)=V_0 e^{-\Delta \omega t} \sin(\omega t+\phi)+a+bt. \quad \text{(Eq. 7)}$$

where a and b are predefined constants that account for the electrical impedance of the wire and also absorb the offset due to unknown background interference.

In the discussion above in connection with FIGS. 2B and 2C, it is noted that FIG. 2B shows vibration of the vibrating wire 102 with a relatively large amplitude and high quality factor, and FIG. 2C shows vibration of the vibrating wire 102 with a lower amplitude and quality factor.

The quality factor (Q) can be computed based on the decrement, $\Delta$ (defined according to Eq. 2), and is expressed as:

$$Q=(2\Delta)^{-1}. \quad \text{(Eq. 8)}$$

As can be seen in Eq. 8, the quality factor, Q, is inversely proportional to the decrement, Δ.

Figure 4:
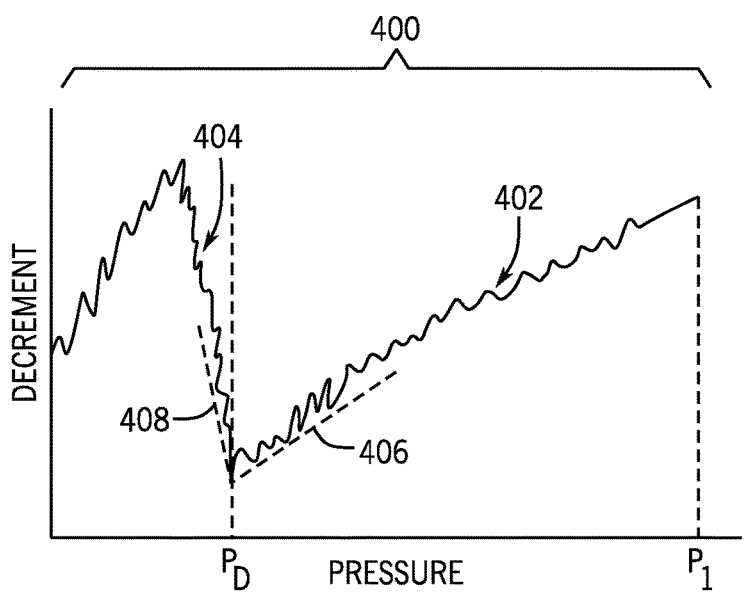
FIG. 4 is a chart depicting values of a decrement as a function of different pressures, according to some implementations.

FIG. 4 is a graph that illustrates an example curve 400 that represents decrement, Δ as a function of pressure. The dew point for a retrograde condensate can be determined during depressurization of the chamber 112 of FIG. 1, by measuring the pressure dependence of the decrement, Δ, which is inversely proportional to the quality factor, Q, of the vibrating wire resonance. As shown in FIG. 4, as pressure is reduced starting at around $P_1$, the decrement, Δ gradually decreases in value with decreasing pressure, as represented by the curve portion 402.

However, once the pressure is reduced below the dew point, $P_D$, the decrement, Δ, rises sharply, as represented by the curve portion 404. As shown in FIG. 4, a line segment 406 represents the fit of certain data points of the curve portion 402, while a line segment 408 represents the fit of certain data points of the curve portion 404. The fitting that can be performed can include a high order polynomial fit, such as a parabolic fit, a cubic fit, and so forth.

The intersection of the line segments 406 and 408 defines the dew point pressure. Stated differently, the dew point is the point along the pressure axis (horizontal axis) at which the slopes of the line segments corresponding to data values of the decrement, Δ, change sign. In the example of FIG. 4, the line segment 406 has a positive slope, and the line segment 408 has a negative slope. Processing of the decrement values yields the line segments 406 and 408, and the processing can look for the change in slope of the line segments 406 and 408.

Figure 5:
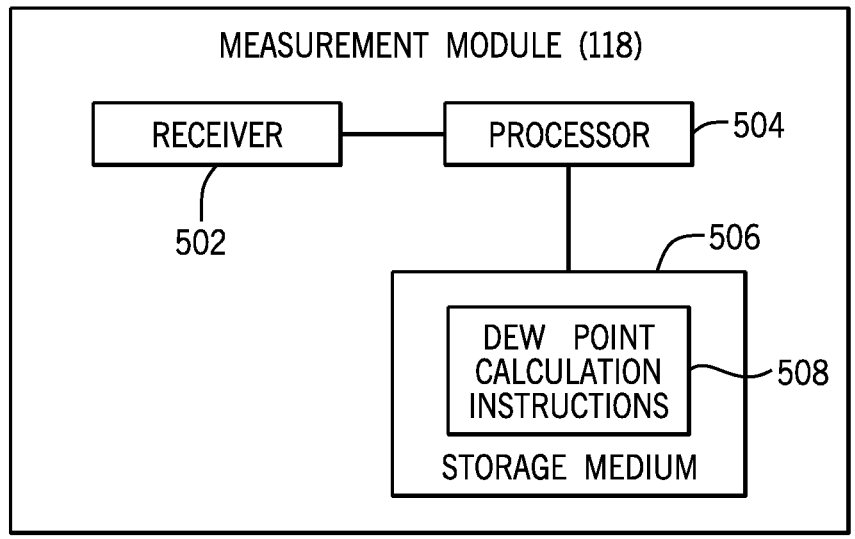
FIG. 5 is a block diagram of an example measurement module, according to some implementations.

FIG. 5 is a block diagram of an example arrangement of a measurement module 118 according to some examples. The measurement module 118 can include a receiver 502 that receives signals corresponding to the vibration of the vibrating wire 102 over the communication lines 116 shown in FIG. 1. The measured data is provided to a processor 504 (or multiple processors). A processor can include a microprocessor, microcontroller, processor module or subsystem, programmable integrated circuit, programmable gate array, or another control or computing device.

The measurement module 118 also includes a non-transitory machine-readable or computer-readable storage medium (or storage media) 506, which can store dew point calculation instructions 508 that are executable on the one or more processors 504. The dew point calculation instructions 508 can determine the dew point based on measurement data acquired by the measurement module 118.

The storage medium (or storage media) 506 can include different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

Figure 6:
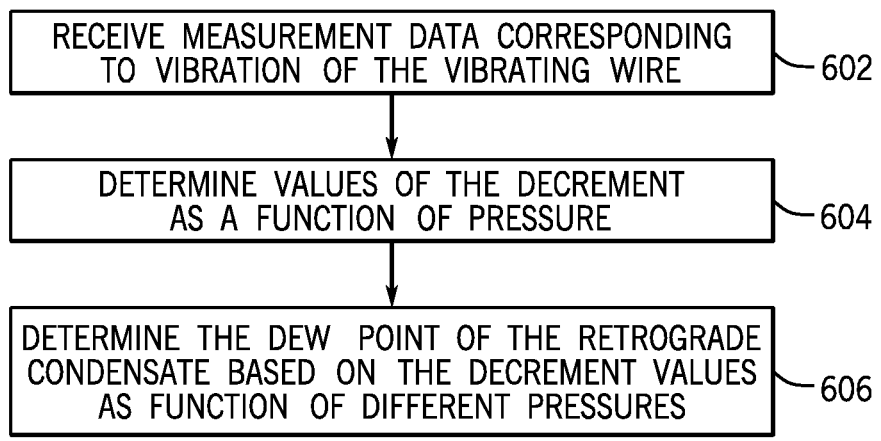
FIG. 6 is a flow diagram of an example process according to some implementations.

FIG. 6 is a flow diagram of a process that can be performed by the dew point calculation instructions 508 according to some implementations. The FIG. 6 process receives (at 602) measurement data corresponding to vibration of the vibrating wire 102. The measurement data includes voltages detected by the measurement module 118 that correspond to the vibratory motion of the vibrating wire 102. The measurement data can be collected across a range of pressures, starting from a higher pressure and proceeding to a lower pressure.

The FIG. 6 process further determines (at 604) values of the decrement, Δ, as a function of pressure, based on the measured data. The decrement is computed according to Eq. 2 set forth above.

Based on the decrement values as a function of different pressures, such as shown in FIG. 4 discussed above, the FIG. 6 process is able to determine (at 606) the dew point of the retrograde condensate that is in the chamber 112 of the vibrating wire viscometer 100 of FIG. 1.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

What is claimed is:

1. A system comprising:
    a sensor device comprising:
        an electrically conductive wire immersible in a fluid in a retrograde condensate;
        support structures to hold the wire, wherein the wire when energized results in vibratory movement of the wire;
        an activator to excite the wire to cause vibration of the wire; and
        a measurement module to measure signals representative of the vibratory movement of the wire, the measurement module is to output measured signals after the excitation of the wire has been removed; and
    at least one processor to determine a dew point of the fluid based on the measured signals from the sensor device, the determining the dew point of the fluid comprises determining values of a decrement relating to motion of the wire across different pressures and identifying a pressure at which a slope of the values of the decrement changes sign.

2. The system of claim 1, wherein the dew point is a pressure at which condensation of the fluid starts to occur.

3. A method for determining a dew point of a fluid in a retrograde condensate, comprising:
    providing a sensor including an outer housing defining a chamber and a vibrating wire in the chamber, wherein the vibrating wire is held in tension;
    introducing the fluid into the chamber, wherein the fluid is in contact with the vibrating wire;
    driving an electrical current into the vibrating wire in a presence of a magnetic field, to create an oscillating force for a vibratory motion of the vibrating wire, wherein the vibratory motion of the vibrating wire is responsive to accumulation of dew droplets on the vibrating wire that lowers a resonant frequency and increases damping of the vibrating wire;

reducing a pressure in the chamber to obtain the measured vibratory motion at different pressures;

determining values of a parameter across the different pressures, wherein the parameter is a decrement relating to the vibratory motion of the vibrating wire; and determining the dew point of the fluid by identifying a pressure at which a slope of the values of the decrement changes sign.

4. The article of claim 3, wherein determining the dew point of the fluid comprises determining a pressure of the fluid at which condensation starts to occur.

5. The article of claim 3, wherein the measured vibratory motion represents a transient response of the vibrating wire in response to excitation of the vibrating wire with the electrical current in a presence of the magnetic field followed by removal of the excitation.

6. An article comprising at least one non-transitory machine-readable storage medium storing instructions that upon execution cause a system to:

introduce a fluid in a retrograde condensate into a vibrating wire viscometer that includes a vibrating wire, wherein the fluid is in contact with vibrating wire;

drive an electrical current into the vibrating wire in a presence of a magnetic field, to create an oscillating force for a vibratory motion of the vibrating wire;

measure a vibratory motion of the vibrating wire from the vibrating wire viscometer at different pressures;

determining values of a parameter across the different pressures, wherein the parameter is a decrement relating to the vibratory motion of the vibrating wire; and determine a dew point of the fluid by identifying a pressure at which a slope of the values of the decrement changes sign.

* * * * *